United States Patent
Cahill

(10) Patent No.: US 10,201,371 B2
(45) Date of Patent: Feb. 12, 2019

(54) SURGICAL DEVICE

(75) Inventor: Ronan Cahill, Dublin (IE)

(73) Assignee: EUROPEAN INSTITUTE OF SURGICAL RESEARCH AND INNOVATION LIMITED, Dublin (IE)

( * ) Notice: Subject to any disclaimer, the term of this patent is extended or adjusted under 35 U.S.C. 154(b) by 155 days.

(21) Appl. No.: 13/984,466

(22) PCT Filed: Feb. 8, 2012

(86) PCT No.: PCT/EP2012/000573
§ 371 (c)(1),
(2), (4) Date: Aug. 9, 2013

(87) PCT Pub. No.: WO2012/113509
PCT Pub. Date: Aug. 30, 2012

(65) Prior Publication Data
US 2013/0324800 A1    Dec. 5, 2013

(30) Foreign Application Priority Data

Feb. 8, 2011    (GB) .................................. 1102163.1

(51) Int. Cl.
| | | |
|---|---|---|
| A61B 17/34 | (2006.01) | |
| A61B 1/32 | (2006.01) | |
| A61M 13/00 | (2006.01) | |
| A61B 17/02 | (2006.01) | |
| A61B 17/00 | (2006.01) | |

(52) U.S. Cl.
CPC ............ *A61B 17/3423* (2013.01); *A61B 1/32* (2013.01); *A61B 17/0293* (2013.01);
(Continued)

(58) Field of Classification Search
CPC ...... A61M 29/00; A61B 1/32; A61B 17/3423; A61B 17/02; A61B 17/3431;
(Continued)

(56) References Cited

U.S. PATENT DOCUMENTS 2,835,253 A * 5/1958 Borgeson ............... A61B 19/38
128/846
3,599,239 A * 8/1971 Tatum ....................... A42B 3/14
2/416

(Continued)

FOREIGN PATENT DOCUMENTS

EP    2168508 A2    3/2010
EP    2181658 A2    5/2010
(Continued)

OTHER PUBLICATIONS

GB Search Report; GB1102163.1; dated Jun. 1, 2011.
PCT International Search Report and Written Opinion; PCT/EP2012/000573; dated Aug. 23, 2012.

*Primary Examiner* — Eric S Gibson
*Assistant Examiner* — Marcela I Shirsat
(74) *Attorney, Agent, or Firm* — Westman, Champlin & Koehler, P.A.; Z. Peter Sawicki; Amanda M. Prose

(57) ABSTRACT

A port for laparoscopic surgery comprises an opening for attachment to a wound protector and a flexible membrane extending therefrom to define an airtight seal around an incision in a patient. A plurality of access points are defined in the membrane, through which laparoscopic trocars and elongate laparoscopic surgical instruments can be inserted.

13 Claims, 3 Drawing Sheets

(52) U.S. Cl.
CPC ............ *A61M 13/00* (2013.01); *A61B 17/02* (2013.01); *A61B 17/3431* (2013.01); *A61B 2017/00907* (2013.01); *A61B 2017/3429* (2013.01); *A61B 2017/3449* (2013.01); *A61B 2017/3466* (2013.01); *A61B 2017/3482* (2013.01); *A61B 2017/3492* (2013.01)

(58) Field of Classification Search
CPC ............ A61B 17/0218; A61B 17/0293; A61B 2017/3482; A61B 2017/3429; A61B 2017/3492; A61B 2017/00907; A61B 2017/00902; A61B 2017/3449; A61B 2017/3466; A61B 2017/3425; A61B 2017/3427; A61B 2017/0225; D05B 91/41; Y10T 16/39; Y10T 29/53661
USPC ........ 600/200, 204, 205, 206, 208, 233, 235
See application file for complete search history.

(56) References Cited

U.S. PATENT DOCUMENTS

| | | | |
|---|---|---|---|
| 5,813,409 A * | 9/1998 | Leahy | A61B 17/3423 128/850 |
| 5,957,913 A * | 9/1999 | de la Torre | A61B 17/3423 606/1 |
| 6,454,783 B1 | 9/2002 | Piskun | |
| 6,485,467 B1 * | 11/2002 | Crook | A61B 17/3423 604/174 |
| 8,920,431 B2 * | 12/2014 | Shibley | A61B 17/0218 606/114 |
| 2002/0038077 A1 * | 3/2002 | de la Torre et al. | 600/203 |
| 2005/0137609 A1 * | 6/2005 | Guiraudon | A61B 17/3423 606/108 |
| 2006/0241651 A1 | 10/2006 | Wilk | |
| 2008/0255519 A1 * | 10/2008 | Piskun | A61B 1/32 604/174 |
| 2009/0187079 A1 | 7/2009 | Albrecht et al. | |
| 2010/0094227 A1 | 4/2010 | Albrecht et al. | |
| 2010/0249694 A1 | 9/2010 | Choi et al. | |
| 2010/0312061 A1 | 12/2010 | Hess et al. | |
| 2011/0172495 A1 * | 7/2011 | Armstrong | 600/233 |

FOREIGN PATENT DOCUMENTS

| | | |
|---|---|---|
| KR | 100975030 B1 * | 8/2010 |
| KR | 100975030 B1 | 8/2010 |
| KR | 20100108318 A | 10/2010 |
| WO | 9610963 A1 | 4/1996 |
| WO | 2007044849 A1 | 4/2007 |
| WO | 2008121294 A1 | 10/2008 |

* cited by examiner

SURGICAL DEVICE

CROSS REFERENCE TO RELATED APPLICATION

This Application is a Section 371 National Stage Application of International Application No. PCT/EP2012/000573, filed Feb. 8, 2012 and published as WO/2012/113509 on Aug. 30, 2012, in English, which is based on and claims the benefit of priority from British patent application GB 1102163.1, filed Feb. 8, 2011, the contents of which are hereby incorporated by reference in their entirety.

BACKGROUND ART

The present invention relates to surgical methods and devices, and in particular to devices and methods for use in laparoscopic surgery. Laparoscopic, or "keyhole" surgery, is a well-known technique whereby elongate surgical instruments are inserted through one or more narrow incisions in the patient (typically 0.5 to 1.5 cm in diameter). Various instruments can be introduced into the patient in this way including scissors, graspers, cutters, energy dissection and sealing devices etc. The surgeon may pick and choose such instruments to suit his purpose. Laparoscopic surgery has several advantages compared to conventional open surgery. The smaller incisions result in reduced abdominal wall injury and hence lessened postoperative pain and wound complications. Patients typically will also have a shorter recovery time.

There are instruments which are critical to the success of any laparoscopic surgery, and which therefore tend to be used in every case and at nearly all times. For example, in order to hold a laparoscopic incision open, provide secure and sterile access to the patient and ensure a sealed space with sufficient pneumoperitoneum to enable working, a "port" or "trocar" containing an air valve is placed into each wound. Additionally the surgeon must have some feedback so he can guide his actions appropriately; in short, he must be able to see what he is doing. A laparoscope provides a suitable imaging mechanism, with currently known types comprising either a charge coupled device (CCD) for insertion directly into the patient or a telescopic lens system that brings the image out of the patient where it can be recorded with a camera. In addition, a fibre optic cable provides light so the laparoscope can be effective and a pump system insufflates the patient with an inert gas (e.g. carbon dioxide), so the instruments have space in which to move.

It is of course critical to the patient's wellbeing that any surgery is carried out in a safe and sterile manner. This principle is especially important when a laparoscopic operation involves the gastrointestinal tract as many of these procedures are 'clean contaminated' or potentially 'contaminated' (as defined by the US National Research Council group, see for example Berard F and Gandon J. "Postoperative wound infections: the influence of ultraviolet irradiation of the operating room and of various other factors" 1964 *Ann. Surg.* 160(Suppl 1) 1-192) and it extends to include any supplementary wounds which are required for the purposes of gastrointestinal specimen extraction, anastomosis formation or stoma creation as part of a laparoscopic operation. Therefore, when such incisions are made a wound protector is often placed into the body wall in order to protect the skin and subcutaneous tissues from microbiological contamination. In cases involving malignancy, this device also acts to shield the wound against tumour cell implantation. For patient benefit, these incisions are often made at the site of one or more of the laparoscopic trocars already made.

The advantages of laparoscopic operations can be maximized by reducing the number of incisions and recent progress in the field of laparoscopic surgery has resulted in many procedures being performed with just a single incision. This is particularly attractive when one larger incision is required anyway for the purposes of specimen extraction, anastomosis formation or stoma creation as maximising the utility of this wound may spare the patient any additional trocar wounds. However, while such surgery has benefits for the patient, the procedure is made more difficult for the surgeon due to the constraints inherent in performing surgery via a confined access.

Several different single incision laparoscopic ports to enable such working are currently available. For example, the "SILS port" (manufactured by Covidien®) comprises a narrow neck of solid plastic with a defined number of holes (three) machined into the plastic. The port is inserted into the incision, and has flanges at either end so that the port is held in place on either side of the incision. Tubes can then be inserted through the holes, and elongate surgical instruments inserted through the tubes to allow their access to the patient. The general construct of the outer interface is similar in other commercially available ports including those made by Advanced Surgical Concepts, Ethicon Endosurgery, Innovia, Applied Medical and Karl Storz. While some of these devices impose strict cylindrical or conical entry and parallel instrumentation, all (including the low profile devices) impose a fulcrum onto the individual trocars as well as a predetermined, fixed distance. Both of these factors significantly limit the freedom and independence of movement possible by the individual instruments and optic. In addition, all are supplied in kits that are restrictive in terms of available trocar number (limiting the number of instruments that can be used at any one time) and dimension (limiting the types of instruments that can be used at any one time) and tend to be exclusive of complementary tools that may be already available in a surgery department but made by a different manufacturer.

For example, many existing ports (such as Covidien's, described above) are manufactured with components comprising relatively hard plastic and have a defined number of access points for instruments. In addition the access points have a defined size, allowing only instruments of a certain diameter to be used. Surgeons therefore have to plan ahead within very narrow confines which instruments they will need for each particular part of the procedure. If a part of the procedure requires five instruments, say, and the port allows only four instruments to access the operating field at any one time, further incisions will be necessary. In addition, the surgeon's ability to improvise is lost (or at least hampered). For instance, he may need to stem excessive bleeding, but be unable to introduce either further instruments or instruments of greater calibre through the existing port. In addition, the relative hard nature of the construction material in currently available single ports limits the range of motion that is possible for the surgeon engaged in simultaneous instrument working—that is, the instruments are held at fixed distances at their fulcrum points in the device atrium. Furthermore, the fixed number of firm or rigid apertures which are moulded a fixed distance apart from each other (a feature common to many currently commercially available single port devices) imposes further constraints on the manoeuvrability and fluency of instrument movement and flow. Because of this firm nature of the material in which the bores or conduits for access are placed, the currently available ports tend also to contain the minimum number of extra conduits as additional non-used access sites further cramp the working space at the port. The only available device that allows maximum freedom of motion within it actually has no physical seal at the port (Airseal by Surgiquest) but is instead very large in its own diameter and physically restrictive.

Finally, all existing ports are relatively expensive. This dissuades medical authorities from authorising single-port laparoscopic techniques, in spite of the potential health benefits to patients and greatly restricts the opportunity for surgeons to gain expertise with these devices. The expense of these devices in practice also prohibits their use as adjuncts to standard multiport laparoscopic procedures (i.e. their use on any potential extraction wound site on a patient). For all these reasons, these devices tend to be used only in highly selected patients in selected centres rather than representing an additional capability for laparoscopic surgery more generally.

SUMMARY OF THE INVENTION

The present invention seeks to address these and other problems.

In one aspect, there is provided a port for laparoscopic surgery comprising an opening for attachment to a laparoscopic wound protector; and a flexible membrane extending from the opening, the membrane providing an air-tight seal around the wound and defining a plurality of instrument access points.

In embodiments of the present invention, the flexible membrane further comprises a resilient ring member around said opening, which allows the port to "snap" on to the ring of a wound protector.

The flexible membrane may comprise a further resilient ring member, coaxially aligned with the first resilient ring member, but laterally displaced therefrom. The second ring member, in combination with the first, provides a degree of stiffness to the port, and limits the port's tendency to twist shut if the procedure requires rotation of the working instruments.

In embodiments of the invention, the membrane has a thickness in the range 0.1 to 2.5 mm, and may be in the range 0.5 mm to 2 mm The membrane may be elastic, as well as flexible. The membrane may be translucent, to allow the surgeon to view the instrument tips entering and exiting the patient cavity.

The membrane can be made from any material which fits the requirements of flexibility and, in some embodiments, elasticity. Suitable examples include natural or synthetic rubber, or silicone.

In an embodiment, the plurality of instrument access points comprises a plurality of tubular extensions of the membrane. When unused, the flexibility and thinness of the membrane means the conduits provide minimal physical obstruction to or interference with instrumentation working in other channels.

In a further aspect of the invention, there is provided a combination of a port for laparoscopic surgery as defined above, and a wound protector comprising third and fourth resilient ring members; and a flexible sleeve connected between the circumferences of the third and fourth ring members.

In an embodiment of this further aspect, the first ring member has an inner diameter which is smaller than the outer diameter of at least one of the third and fourth resilient ring members, allowing the snap fit described above.

In a yet further aspect, there is provided a method of performing laparoscopic surgery, comprising introducing a wound protector to an incision in a patient; attaching a laparoscopic port to the wound protector, the port comprising an opening for attachment to the wound protector and a flexible membrane extending from said opening, said membrane providing an air-tight seal around the wound and defining a plurality of instrument access points; and inserting a surgical instrument and/or trocar through one of said instrument access points.

Once the instrument/trocar is inserted through the instrument access point, it may be tied off to ensure an airtight seal. Use of the same material as the membrane achieves a particularly good seal.

One of the instrument access points may be such so as to allow insertion of a pump and insufflation of a body cavity inside said incision. The channel for air sufflation may be placed and configured separately from the conduits used primarily for instrument insertion.

After insufflation, the port comprises an intra-device space which is external to the body cavity. That is, the port is inflated and remains outside the patient, allowing plenty of room for the instruments to manoeuvre.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
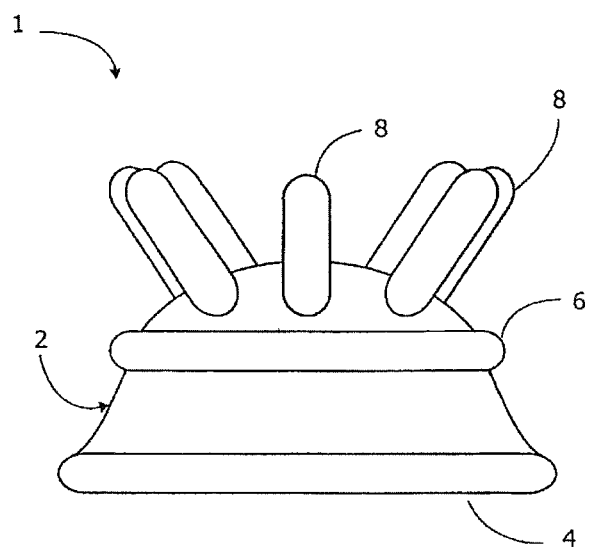
FIGS. 1 and 2 show a surgical device according to embodiments of the present invention in side and plan views, respectively.
Figure 2:
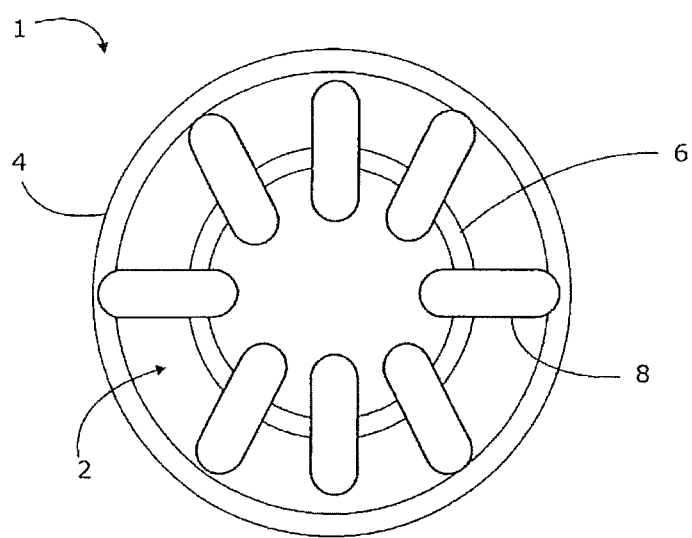

FIG. 1 shows a laparoscopic port 1 according to embodiments of the invention. FIG. 2 shows the same port in plan view.

The port 1 comprises a generally dome-shaped membrane 2 which, in use, sits over a wound protector placed in an incision made in the patient (typically in the abdomen, although the port is applicable to many different parts of the body including transanal intraluminal operations), and creates an airtight seal between the inside of the patient and the inside of the proposed port. A flexible, resilient ring member 4 defines an opening which is to be placed around the external component of the wound protector. In the illustrated embodiment that opening is circular due to its simplicity of manufacture, but alternative shapes may be employed.

The wound protector serves to protect the sides of the incision from damage by surgical instruments inserted therethrough. In addition, however, it may also serve to retract the incision, i.e. to hold the wound open. Hereinafter, the term "wound protector" is used to describe any apparatus which can be inserted into an incision made in a patient, and which protects and/or retracts the incision during laparoscopic surgery.

The membrane 2 extends inwardly from the ring member 4 in a dome or cylindrical shape towards a second ring member 6. That ring member 6 may have a smaller diameter than the lower ring member 4, but otherwise the two members have a similar construction. As will be described in greater detail below, the lower ring member 4 allows greater sealing of the port 1 onto a wound protector in the abdominal wall. The second ring member 6, in conjunction with the first ring member 4, provides a degree of stiffness to the port 1 that reduces and/or prevents it from being twisted off the wound protector and also limits the port's tendency to twist shut if the procedure requires rotation of the working instruments.

The membrane 2 continues to extend in a dome shape, and ultimately forms a hollow, flexible cup. Inside the diameter of the upper ring member 6 are formed several instrument access points 8. In the illustrated embodiment there are eight such access points 8, but again one skilled in the art will appreciate that more or fewer access points may be provided without departing from the scope of the invention. Each access point 8 is a hollow, tubular extension of the membrane away from its otherwise dome shape. In embodiments of the present invention, the access points may be distributed approximately equally around the upper parts of the port 1, to allow the surgical instruments inserted therethrough as much space to manoeuvre as possible. One access point may of course also be used specifically to provide for gas sufflation.

In an embodiment the membrane 2 is see-through, that is, sufficiently translucent that a surgeon can see the instruments safely entering the patient through the membrane material. In such embodiments, the membrane will in general not be completely transparent, having an optical density such to limit the nuisance associated with loss of laparoscopic light from within the abdominal cavity.

In embodiments of the present invention, the device construction allows conventional manufacturing processes to be used, including for example mould dipping or injection moulding. Further, the device construction should allow the device to be sterilised. Those skilled in the art will appreciate that the exact dimensions of the device will vary with regard to differing potential procedures within its scope and the dimensions of already existing wound protectors. The optimum material for construction is one that is thin, flexible and elastic yet durable. Therefore natural or synthetic rubber could be used as could silicone. In one embodiment, the membrane 2 has a thickness in the range 0.1 mm to 2.5 mm; a narrower range of 0.5 mm to 1 mm is optimal. The ring components could be composed of thickened or plicated segments of the membrane material used or indeed from separate inserts that could be placed after construction of the device mould FIGS. 3a to 3d show different stages of a laparoscopic surgical procedure according to embodiments of the present invention.

Figure 3A:
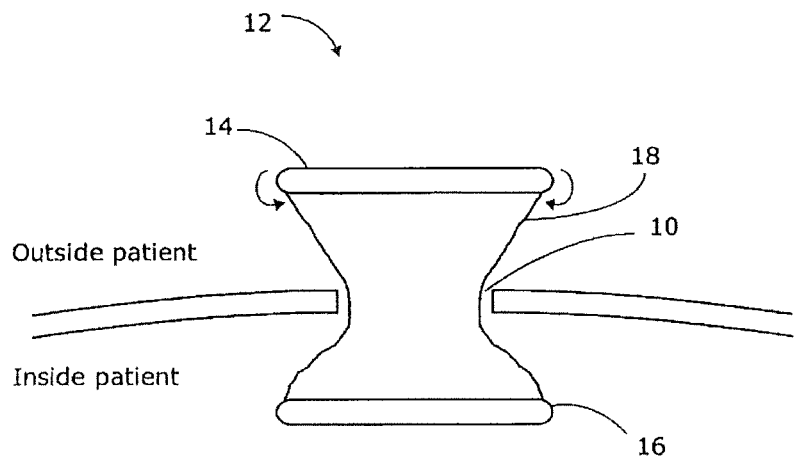
FIGS. 3a to 3d show the different stages of a laparoscopic surgical procedure using a surgical device according to embodiments of the present invention.
Figure 3B:
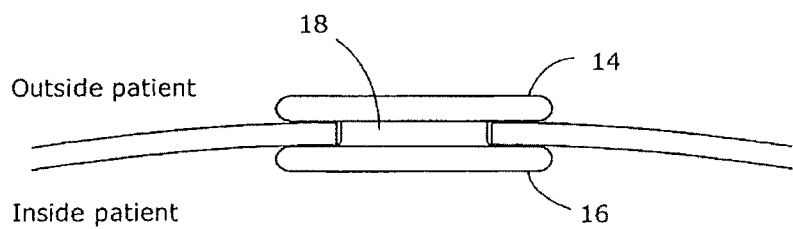

FIGS. 3a and 3b show application of a wound protector 12 to an incision 10 in a patient. The wound protector 12 comprises two flexible, resilient rings 14, 16, and a flexible sleeve of material 18 connected between the respective circumferences of the two rings.

After an incision 10 is made, one of the flexible rings 16 is deformed and inserted therethrough (FIG. 3a). Once inside the patient, the resilient ring 16 returns to its original diameter such that it cannot easily be pulled out through the incision.

At this stage, the outer ring 14 is twisted over and over on itself as shown in FIG. 3a. This has the effect of shortening the sleeve 18 and therefore bringing the rings 14, 16 closer together, until eventually they form a tight grip on the wall of the patient surrounding the incision 10 (see FIG. 3b). The wound protector 12 therefore keeps the incision (wound) open and protects the wound from damage by the surgical instruments that will be used in the patient. They have also been shown to reduce the rate of infection in patients.

Figure 3C:
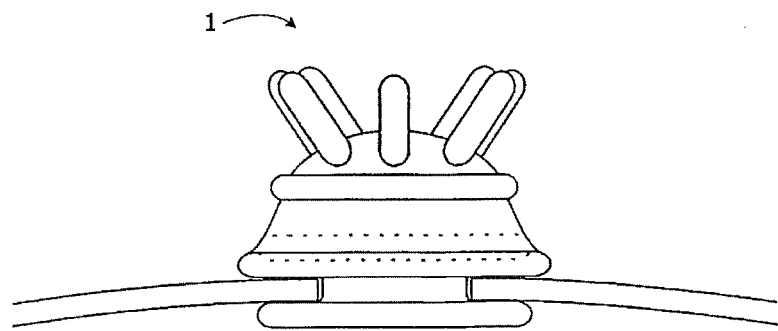

FIG. 3c shows the application of a port 1 according to embodiments of the present invention to the wound protector 12 described above. The wound protector's external ring member 14 is shown in dashed lines as it is obscured from view by the port 1. The inner diameter of the port's lower ring member 4 is sized to be smaller than the outer diameter of the wound protector's external ring member 14. That is, the lower ring member of the port must be stretched over the ring member 14 of the wound protector. Once stretched over, the resilient ring member 4 returns to its original diameter, effectively snapping on to the wound protector. This achieves an airtight seal around the incision 10, between the insides of the patient and the atmosphere. In addition, this mechanism of attachment allows the port device to rotate with the wound protector in situ.

As mentioned above, a pump system (not illustrated) is usually employed to insufflate the patient with an inert gas (e.g. carbon dioxide). The seal between the port 2 and the wound protector-retractor 14 must therefore be strong enough to keep the gas inside the patient. The relative diameters of the ring members 4, 14 and their respective resilience are therefore chosen carefully so that the port 1 can be fitted to the wound protector 12 without excessive difficulty, but also so that the fit is sufficiently tight that the port 1 remains in place despite the pressure difference between the insides of the patient (when inflated) and outside, and despite flexing of the port due to movement by the surgeon. Alternative connection mechanisms may be employed by those skilled in the art without departing from the scope of the invention, but the present embodiment is considered to be cheap, easily manufactured and effective.

Figure 3D:
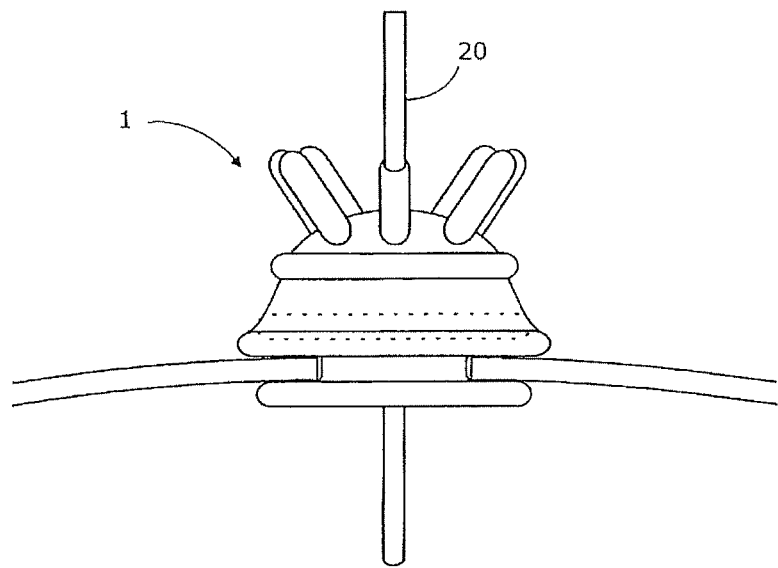

FIG. 3d shows a stage of the operation where an elongate laparoscopic surgical instrument 20 has been inserted through one of the access points 8. The end of the access point 8 is simply cut or punctured with a suitable instrument (e.g. scissors), and the instrument 20 inserted through. Alternatively, and especially where repeated instrument exchanges are required (e.g. swapping a graspers for a scissors), a laparoscopic trocar can be inserted into the conduit and fixed in position allowing more fluent, convenient and efficient (especially in terms of minimised gas leak) operative progress.

Again, an airtight seal must be achieved by the port, despite the puncture at the access point 8. The membrane 2 will in general have some resilience, and in some embodiments this is sufficient to provide an airtight seal around the instrument 20. However, in other cases it may be necessary to tie off the access point around the instrument 20 or positioned trocar, with string or elastic, or any other suitable material. Use of the same material as that in the membrane 2 has been shown to achieve a good seal.

It may also be advantageous to provide valves (not illustrated) at each of the access points 8 to allow extraction of the surgical instrument 20 without affecting the airtight seal around the wound.

The present invention therefore provides a port for laparoscopic surgery, providing an airtight seal around a wound protector placed in an incision, but allowing easy access for laparoscopic surgical instruments. In short, a simple membrane is stretched over a wound protector surrounding the incision. The membrane has a plurality of access points defined in it, each allowing ingress of a laparoscopic surgical instrument. The port is cheap compared to existing solutions, but also extremely effective. Because it is compatible with wound protectors/retractors already in use, it can be used across a broad spectrum of patient sizes and habituses. It can allow a large number of instruments access to the patient, and places only very limited constraints on the diameter of those instruments, such that surgeons are left free to alter operative flow or improvise if necessary during a surgical procedure, relieving the surgeon of any pressure of highly rarefied preselection criteria for use of this approach. Furthermore, the device is non-prescriptive in terms of which trocars or instruments are used in associated with this access device allowing it to complement those already present in and familiar to individual surgeons and departments. The nature of the material also places minimal restriction on the range of movements of the instruments available to the surgeon (i.e. there is considerable degree of freedom in each of the vertical, horizontal and rotational planes). In addition, the flexible nature of the membrane, and in particular the dome component onto which the conduits are mounted, allows great freedom of independent movement of simultaneously working instruments and their sheaths or trocars. Finally, because the 'contained' space within the port is in fact external to the patient, a variety of needle trocars (including reuseable, reposable and disposable and both shielded and non-shielded systems) can be safely used with this device without risk of internal organ or tissue injury.

It will of course be understood that many variations may be made to the above-described embodiment without departing from the scope of the present invention.

The invention claimed is:

1. A port for laparoscopic surgery, comprising:
an opening having a first flexible, resilient ring member around said opening for attachment to a laparoscopic wound protector;
a second flexible, resilient ring member having a smaller diameter than the first flexible, resilient ring member and being laterally displaced from the first flexible, resilient ring member; and
a flexible membrane forming a hollow, flexible, generally dome-shaped cup, said membrane providing an air-tight seal around the wound, the membrane extending inwardly from the first flexible, resilient ring member towards said second flexible, resilient ring member, the second flexible, resilient ring member extending around the exterior of the dome-shaped cup, the dome-shaped cup within the second flexible, resilient ring member having defined in it a plurality of instrument access points, the port being a single integral piece.

2. The port according to claim 1, wherein the second flexible, resilient ring member is coaxially aligned with the first flexible, resilient ring member.

3. The port according to claim 1, wherein the membrane has a thickness in the range 0.1 to 2.5 mm.

4. The port according to claim 1, wherein the plurality of instrument access points comprises a plurality of tubular extensions of the membrane.

5. The port according to claim 1, wherein the membrane is elastic.

6. The port according to claim 1, wherein the membrane is translucent.

7. The port according to claim 1, wherein the membrane comprises natural or synthetic rubber or silicone.

8. The combination of a port for laparoscopic surgery according to claim 1, and a wound protector comprising:
third and fourth flexible, resilient ring members; and
a flexible sleeve connected between the circumferences of the third and fourth ring members.

9. The combination according to claim 8, wherein the first ring member has an inner diameter which is smaller than the outer diameter of at least one of the third and fourth flexible, resilient ring members.

10. A method of performing laparoscopic surgery, comprising:
introducing a wound protector to an incision in a patient;
attaching a laparoscopic port to the wound protector, the port comprised of a single integral piece and comprising an opening having a first flexible, resilient ring member around said opening for attachment to the wound protector, a second flexible, resilient ring member having a smaller diameter than the first flexible, resilient ring member and being laterally displaced from the first flexible, resilient ring member, and a flexible membrane forming a hollow, flexible, generally dome-shaped cup, said membrane providing an air-tight seal around the wound, the membrane extending inwardly from the first ring member in a dome or cylindrical shape towards said second flexible, resilient ring member, the second flexible, resilient ring member extending around the exterior of the dome-shaped cup, the dome-shaped cup within the second flexible, resilient ring member having defined in it a plurality of instrument access points; and inserting a surgical instrument and/or trocar through one of said instrument access points.

11. The method according to claim 10, further comprising:
tying off the instrument access point using the same material as the membrane.

12. The method according to claim 10, further comprising:
inserting a pump through one of said instrument access points and insufflating a body cavity inside said incision.

13. The method according to claim 12, wherein, after insufflation, the port comprises an intra-device space which is external to the body cavity.

* * * * *